United States Patent
Wince et al.

(10) Patent No.: US 11,594,312 B2
(45) Date of Patent: Feb. 28, 2023

(54) DATA AGGREGATION AND PROCESS AUTOMATION SYSTEMS AND METHODS

(71) Applicant: Myndshft Technologies, Inc., Dover, DE (US)

(72) Inventors: Ronnie Wince, Mesa, AZ (US); Tyler Wince, Mesa, AZ (US)

(73) Assignee: Myndshft Technologies, Inc, Mesa, AZ (US)

( * ) Notice: Subject to any disclaimer, the term of this patent is extended or adjusted under 35 U.S.C. 154(b) by 511 days.

(21) Appl. No.: 16/570,268

(22) Filed: Sep. 13, 2019

(65) Prior Publication Data

US 2020/0090799 A1 Mar. 19, 2020

Related U.S. Application Data

(60) Provisional application No. 62/732,968, filed on Sep. 18, 2018.

(51) Int. Cl.
| | |
|---|---|
| *G16H 10/60* | (2018.01) |
| *G16H 15/00* | (2018.01) |
| *H04L 9/06* | (2006.01) |
| *G06Q 20/42* | (2012.01) |
| *G16H 40/20* | (2018.01) |

(52) U.S. Cl.
CPC ............. *G16H 15/00* (2018.01); *G06Q 20/42* (2013.01); *G16H 40/20* (2018.01); *H04L 9/0637* (2013.01)

(58) Field of Classification Search
CPC ........ G16H 15/00; G16H 40/20; G16H 10/60; G06Q 20/42; G06Q 2220/00; G06Q 20/02; G06Q 20/065; G06Q 20/223; G06Q 20/3678; G06Q 20/3827; G06Q 20/3829; G06Q 20/389; H04L 9/0637; H04L 63/08; H04L 2209/38; H04L 2209/88; H04L 2463/102; H04L 9/3239
See application file for complete search history.

(56) References Cited

U.S. PATENT DOCUMENTS

| | | |
|---|---|---|
| 7,596,576 B2 | 9/2009 | Venkatesh et al. |
| 8,843,997 B1 | 9/2014 | Hare |
| | (Continued) | |

FOREIGN PATENT DOCUMENTS

| | | |
|---|---|---|
| WO | 2018007828 | 1/2018 |

*Primary Examiner* — Maroun P Kanaan
(74) *Attorney, Agent, or Firm* — Booth Udall Fuller, PLC

(57) ABSTRACT

A data aggregation and process automation (DAPA) system is disclosed. The DAPA system includes an authentication module, a monitoring module, an intelligent automation module, and a transformation module. The authentication module is configured to initiate authenticated communication with a plurality of servers, and includes an authentication storage having a plurality of authentication credentials and routing information. The monitoring module is configured to monitor a first server for a first change event and monitor a second server for a second change event. The first change event results in the receipt of a first data object and the second change event results in the receipt of a second data object. The intelligent automation module is configured to identify the second server, request a service, and submit an update data object to the first server. The transformation module is configured to transform data objects from one format into another.

20 Claims, 7 Drawing Sheets

(56) References Cited

U.S. PATENT DOCUMENTS

| | | | |
|---|---|---|---|
| 2010/0241595 A1* | 9/2010 | Felsher | G06Q 10/10 |
| | | | 705/400 |
| 2011/0161111 A1* | 6/2011 | Dicks | A61B 5/0022 |
| | | | 705/3 |
| 2016/0125166 A1 | 5/2016 | Raja | |
| 2020/0020424 A1* | 1/2020 | Lin | G16H 10/60 |

* cited by examiner

DATA AGGREGATION AND PROCESS AUTOMATION SYSTEMS AND METHODS

RELATED APPLICATIONS

This application claims the benefit of U.S. provisional patent application 62/732,968, filed Sep. 18, 2018 titled "Data Aggregation and Process Automation Systems and Methods," the entirety of the disclosure of which is hereby incorporated by this reference.

TECHNICAL FIELD

Aspects of this document relate generally to data aggregation and process automation.

BACKGROUND

Many industries, such as healthcare, are built upon a number of different organizations that must all work together, despite sometimes having divergent business interests and often using incompatible infrastructure and systems. Often, these organizations utilize legacy systems that have been built up over a period of many years, at great cost. Because of this, adoption of new systems and integration with other legacy systems is limited. Even with the use of trust-agnostic networks such as permissioned blockchain, the legacy systems and procedures of each organization must be translated and consolidated quickly, or any benefits from the trust-agnostic network will be lost to inefficiencies in interfacing with the network.

For example a healthcare provider, such as a hospital, frequently interacts with healthcare payers such as insurance companies, as well as other healthcare providers like pharmacies and laboratories. Each of these organizations has internal systems for executing their portion of the healthcare revenue cycle. Because of divergent business interests, as well as divergent architectures and protocols, these systems are rarely exposed to other players in the healthcare industry, to the detriment of all.

SUMMARY

According to one aspect, a data aggregation and process automation (DAPA) system includes an authentication module configured to initiate authenticated communication with a plurality of servers communicatively coupled to the DAPA system. The authentication module includes an authentication storage having a plurality of authentication credentials and routing information for each of the plurality of servers. Each of the plurality of servers is associated with a different party. The plurality of servers includes a healthcare provider server associated with a healthcare provider and a healthcare payer server associated with a healthcare payer. The DAPA system also includes a monitoring module configured to monitor the provider server for a change-in-treatment event after receiving authenticated access to the provider server through the authentication module. The monitoring module is further configured to monitor the payer server for a change-in-authorization event after receiving authenticated access to the payer server through the authentication module. The change-in-treatment event is the entry of one of a new medical procedure, a modified medical procedure, a new prescription, and a modified prescription in the provider server and results in the receipt of a treatment data object in a first server format utilized by the provider server. The change-in-authorization event results in the receipt of an authorization data object in a second server format utilized by the payer server. The treatment data object identifies the healthcare payer and includes a patient identity. The DAPA system also includes an intelligent automation module configured to automatically identify the payer server using the treatment data object and the authentication storage in response to the receipt of the treatment data object by the monitoring module, and establish authenticated access to the payer server using the authentication module. The intelligent automation module is further configured to request a prior authorization determination from the payer server by submitting a request data object including at least the patient identity. Said request data object is in the second server format and is based on the treatment data object. Lastly, the intelligent automation module is configured to automatically submit an update data object to the provider server in response to the receipt of the authorization data object by the monitoring module. Said update data object is in the first server format, is based on the authorization data object, and indicates one of a grant of prior authorization and a denial of prior authorization. Lastly, the DAPA system includes a transformation module including a transformation storage having a plurality of data format schema including a first server format schema describing the first server format utilized by the provider server and a second server format schema describing the second server format utilized by the payer server. The transformation module is configured to transform the treatment data object in the first server format into the request data object in the second server format, and further configured to transform the authorization data object in the second server format into the update data object in the first server format.

Particular embodiments may comprise one or more of the following features. At least one of the provider server and the payer server may be a peer on a permissioned blockchain network. The intelligent automation module may be further configured to invoke a smart contract within the permissioned blockchain network. The DAPA system may be executed within a containerized computing environment. The authentication storage and the transformation storage may exist within the same database. The monitoring module may be configured to monitor the provider server and the payer server using at least one of long polling, publication/subscription messaging, and periodic queries. At least one of the provider server and the payer server may be one of a revenue cycle management system, an electronic medical record system, an electronic health record system, and a database.

According to another aspect of the disclosure, a data aggregation and process automation (DAPA) system includes an authentication module configured to initiate authenticated communication with a plurality of servers communicatively coupled to the DAPA system. The authentication module includes an authentication storage having a plurality of authentication credentials and routing information for each of the plurality of servers. Each of the plurality of servers is associated with a different party, the plurality of servers including a first server associated with a first party and a second server associated with a second party. The DAPA system also includes a monitoring module configured to monitor the first server for a first change event after receiving authenticated access to the first server through the authentication module, and further configured to monitor the second server for a second change event after receiving authenticated access to the second server through the authentication module. The first change event is the entry of one of a new medical procedure, a modified medical procedure, a new prescription, and a modified prescription in the first server and results in the receipt of a first data object in a first server format utilized by the first server. The second change event results in the receipt of a second data object in a second server format utilized by the second server. The first data object identifies the second party and includes a patient identity. The DAPA system further includes an intelligent automation module configured to automatically identify the second server using the first data object and the authentication storage in response to the receipt of the first data object by the monitoring module, and establish authenticated access to the second server through the authentication module. The intelligent automation module is further configured to request a service from the second server by submitting a request data object including the patient identity. Said request data object being in the second server format and based on the first data object. The service requested from the second server is one of a prior authorization determination and a verification of benefits and coverage. Finally, the intelligent automation module is configured to automatically submit an update data object to the first server in response to the receipt of the second data object by the monitoring module, said update data object being in the first server format and based on the second data object. Lastly, the DAPA system includes a transformation module having a transformation storage with a plurality of data format schema including a first server format schema and a second server format schema. The transformation module is configured to transform the first data object in the first server format into the request data object in the second server format, and is further configured to transform the second data object in the second server format into the update data object in the first server format. The first party is a healthcare provider and the second party is a healthcare payer.

Particular embodiments may comprise one or more of the following features. At least one of the first server and the second server may be a peer on a permissioned blockchain network. The monitoring module may be configured to monitor the first server and/or the second server using at least one of long polling, publication/subscription messaging, and periodic queries. At least one of the first server and the second server may be one of a revenue cycle management system, an electronic medical record system, an electronic health record system, and a database.

According to yet another aspect of the disclosure, a data aggregation and process automation (DAPA) system includes an authentication module configured to initiate authenticated communication with a plurality of servers communicatively coupled to the DAPA system. The authentication module includes an authentication storage having a plurality of authentication credentials and routing information for each of the plurality of servers. Each of the plurality of servers is associated with a different party, the plurality of servers including a first server associated with a first party and a second server associated with a second party. The DAPA system also includes a monitoring module configured to monitor the first server for a first change event after receiving authenticated access to the first server through the authentication module, and further configured to monitor the second server for a second change event after receiving authenticated access to the second server through the authentication module. The first change event results in the receipt of a first data object in a first server format and the second change event results in the receipt of a second data object in a second server format. The first data object identifies the second party. The DAPA system further includes an intelligent automation module configured to automatically identify the second server using the first data object and the authentication storage in response to the receipt of the first data object by the monitoring module, and establish authenticated access to the second server through the authentication module. The intelligent automation module is also configured to request a service from the second server by submitting a request data object, said request data object being in the second server format and based on the first data object. Lastly, the intelligent automation module is configured to automatically submit an update data object to the first server in response to the receipt of the second data object by the monitoring module, said update data object being in the first server format and based on the second data object. Finally, the DAPA system includes a transformation module having a transformation storage with a plurality of data format schema including a first server format schema and a second server format schema. The transformation module is configured to transform the first data object in the first server format into the request data object in the second server format, and further configured to transform the second data object in the second server format into the update data object in the first server format.

Particular embodiments may comprise one or more of the following features. The first data object may include a patient identity. The service requested from the second server may be a prior authorization determination, and the request data may include the patient identity. The service requested from the second server may be a verification of benefits and coverage, and the request data may include the patient identity. The first change event may include the entry of one of a new medical procedure, a modified medical procedure, a new prescription, and a modified prescription into the first server. The first party may be a healthcare provider and the second party may be a healthcare payer. At least one of the authentication module, the monitoring module, the intelligent automation module, and the transformation module may be executed in a separate containerized environment. The authentication storage and the transformation storage may exist within the same database.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
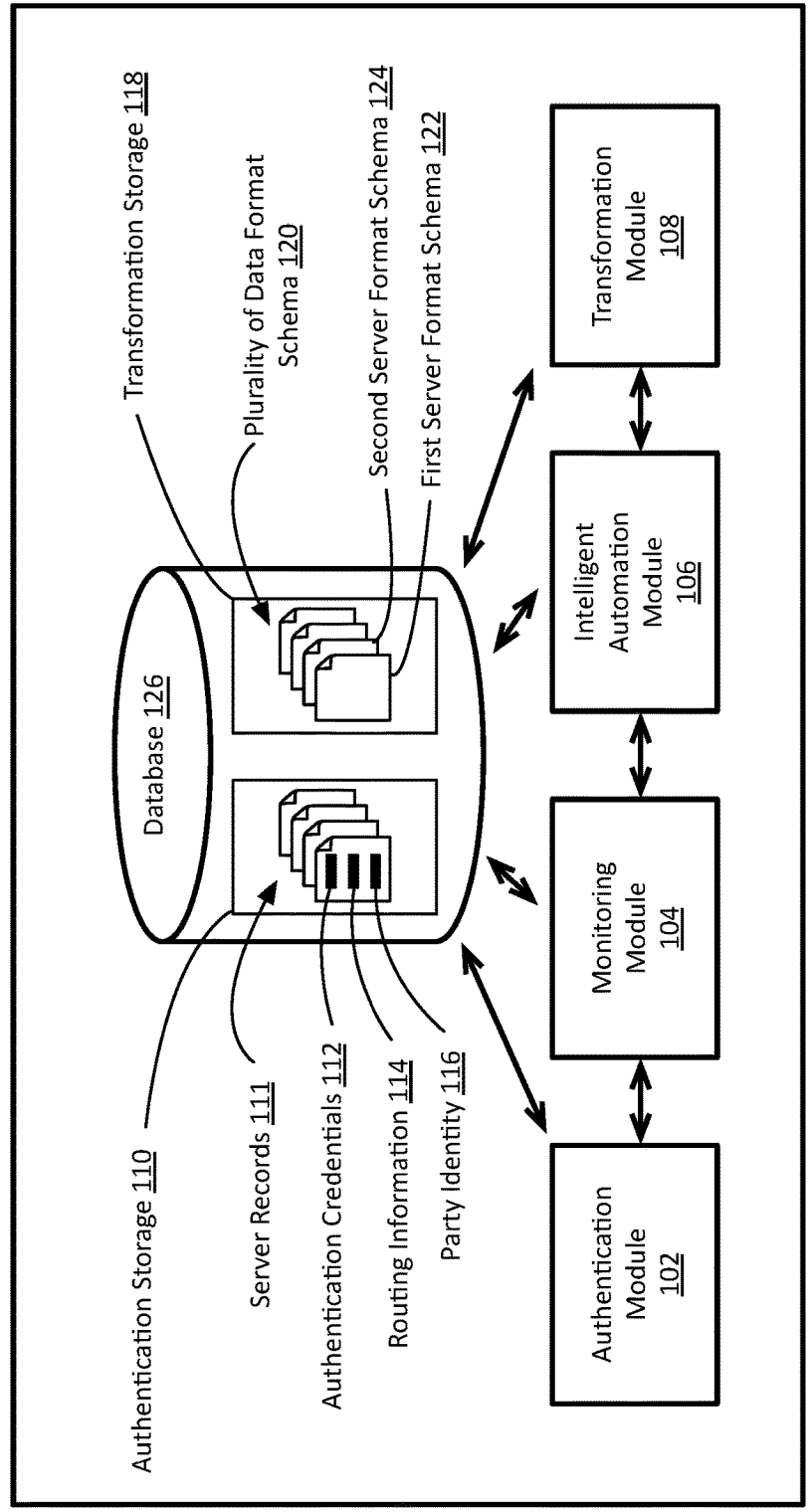
FIG. 1 is a system view of a data aggregation and process automation (DAPA) system.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Many industries, such as healthcare, are built upon many different organizations that must all work together, despite sometimes having divergent business interests and often using incompatible infrastructure and systems. Often, these organizations utilize legacy systems that have been built up over a period of many years, at great cost. Because of this, adoption of new systems and integration with other legacy systems is limited. Even with the use of trust-agnostic networks such as permissioned blockchains, the legacy systems and procedures of each organization must be translated and consolidated quickly, or any benefits from the trust-agnostic network will be lost to inefficiencies in interfacing with the network.

For example, a healthcare provider, such as a hospital, frequently interacts with healthcare payers such as insurance companies, as well as other providers like pharmacies and laboratories. Each of these organizations has internal systems for executing their portion of the healthcare revenue cycle. Because of divergent business interests, as well as divergent architectures and protocols, these systems are rarely exposed to other players in the healthcare industry, to the detriment of all.

Contemplated herein is a data aggregation and process automation (hereinafter DAPA) system and method, able to interface with a multitude of systems, even systems using vastly different data formats and communication protocols, to facilitate and even automate their interaction with each other, and/or interaction with new systems and networks. As a non-limiting example, Myndshft Technologies, Inc., has a DAPA system that is known under the trademark M:IA™. The DAPA system may further be used to automate certain processes, automatically determining what information is needed to accomplish a task, interfacing with various systems to obtain that information, and ultimately place it in a consolidated, usable format. The DAPA system may further be used to input new or modified data into legacy systems as a result of other operations and evaluations.

According to various embodiments, the DAPA system may be configured to access data from a variety of sources known in the art including, but not limited to, SaaS platforms and applications, portals, HIS, EMR/EHR systems, revenue cycle management systems, and the like. In some embodiments the DAPA system may employ artificial intelligence to quickly adapt to the particular data format of a system, reducing the configuration time for quicker implementation and lowering the barrier for integration with legacy systems.

In addition to performing data collection, entry, and transactions between systems, the DAPA system may also be used to maintain up-to-date status of legacy systems operating in concert with modern and even bleeding edge systems. For example, in some embodiments, the DAPA system may monitor a legacy system for new data, or a change in state, and in response immediately take an action (e.g. input new data into another system, make a request, refactor and/or validate data, etc.). As a specific example, the DAPA system may be used to automate the back-and-forth communications between a healthcare provider server and a healthcare payer server while seeking prior authorization for a particular treatment prescribed for a particular patient.

FIG. 1 is a system view of a non-limiting example of a DAPA system. As shown, the DAPA system 100 comprises an authentication module 102, a monitoring module 104, an intelligent automation module 106, a transformation module 108, and at least one storage, such as a database 122. Each element will be discussed in turn.

In the context of the present description and the claims that follow, a module is a collection of routines and functionalities sharing a theme, or a particular piece of infrastructure. The functionalities and routines of the various modules that make up a DAPA system 100 will be discussed in detail below. However, it is worth noting that such delineations should not be interpreted as limiting the overall architecture of a DAPA system 100. For example, in one embodiment, these modules may be implemented as different subroutines within a collection of software instructions that make up a DAPA system 100. In another embodiment, each module may be implemented as a separate executable object within a containerized or virtualized environment. In still another embodiment, one or more of the modules may be implemented as a separate system that is communicatively coupled with the other modules. In some embodiments the modules may be localized to the same hardware environment, while in other embodiments, one or more of the modules may be remote, possibly communicating with the other modules through the Internet.

As shown, the DAPA system 100 comprises an authentication module 102. In the context of the present description and the claims that follow, an authentication module 102 is a module responsible for gaining access to the various servers, systems, devices, networks, etc. that the DAPA system 100 will interact with. More specifically, the authentication module 102 is configured to initiate authenticated communication with a variety of servers that are communicatively coupled to the DAPA system 100.

In some embodiments, the authentication module 102 may simply be responsible for initiating an authenticated connection with a server. For example, in one embodiment, the authentication module 102 may be instructed to connect to a particular server. Once that connection is established, the authentication module 102 may pass that link on to another module for further use. For example, the authentication module 102 may open a network socket, then pass it on to another module. In other embodiments, the authentication module 102 may serve as the mouthpiece of the DAPA system 100, meaning that all communication with other systems, servers, and networks passes through the authentication module 102, and that the nature of the communication (e.g. protocol, etc.) is hidden from the other modules, making the authentication module 102 a black box as far as the other modules are concerned. In still other embodiments, a mix of these two approaches may be implemented, wherein the authentication module 102 can serve as the spokesman for the DAPA system 100 while also being able to return a network socket to another process or module.

It should be noted that many of the modules of the DAPA system 100 are described as being "configured to" perform certain functions or exhibit certain behaviors. Those skilled in the art will recognize that such "configuration" may be implemented through precompiled source code, through code or scripting evaluated at run time, or both. Some aspects of the DAPA system 100 may be fundamental and static, while others may be readily customized for particular functions. This is one of the advantages the DAPA system 100 provides over conventional methods of bridging systems; it can be adapted for use with new systems, even systems not yet developed, without requiring an overhaul of the entire system.

According to various embodiments, the authentication module 102 also comprises an authentication storage 110, which is used to store server records 111 comprising the information the authentication module 102 needs to establish authenticated communication with the various servers. In some embodiments, the authentication storage 110 may be a separate storage resource that is localized to the authentication module 102 (e.g. isolated from other modules, etc.), while in other embodiments, the authentication storage 110 may be implemented using a shared storage resource. For example, as shown in FIG. 1, the authentication storage 110 may be implemented within a database 126 that is also housing a transformation storage 118 that is part of the transformation module 108. Those skilled in the art will recognize the wide range of ways that the authentication storage 110 may be implemented.

The authentication storage 110 comprises authentication credentials 112 (e.g. tokens, passwords, account information, public/private encryption keys, etc.) and routing information 114 (e.g. IP addresses, domain names, ports, protocols, etc.) for each of the plurality of servers the authentication module 102 can communicate with, according to various embodiments. For each of these servers, the authentication storage 110 also comprises an associated party identity 116, allowing the routing information 114 to be resolved from the name of the party associated with a particular server, using the authentication module 102. As a specific example, in an embodiment of the DAPA system being used to bridge the gap between a healthcare provider server and a healthcare payer server, the provider server may be able to identify the name of a patient's health insurance provider, but might not also include the domain name of their public facing records server. Using the authentication module 102 to resolve routing information 114 from a party identity 116 allows the DAPA system 100 to bridge servers that in reality know very little about each other, aside from the identity of who (e.g. individual, corporate entity, etc.) they would like to communicate with. According to various embodiments, some or all of this information may be stored on a plurality of server records 111 within the authentication storage 110. As a specific example, in one embodiment, the server records 111 may be records in a relational database.

The DAPA system 100 also comprises a monitoring module 104. In the context of the present description and the claims that follow, a monitoring module 104 is a module responsible for observing a system to determine if a particular event has occurred and, upon determining that said event has occurred, take appropriate action, either directly or via another module within the DAPA system 100. Some servers may have the ability to notify other systems of the occurrence of certain events, such as a change in a piece of data, the creation of new data, and the like. For example, some servers may have publication/subscription messaging, as is known in the art. According to various embodiments, the monitoring module 104 is tasked with receiving such notifications, and then taking or triggering a predefined action in response to said notification. However, some servers may lack this notification ability. In some embodiments, the monitoring module 104 may be able to actively monitor another system or server for the occurrence of a particular event. After receiving authenticated access to the server (e.g. through the authentication module 102, etc.), the monitoring module 104 may employ long polling (e.g. maintaining active access to the system for a period of time to watch for the event, etc.), periodic queries (e.g. periodically requesting an update from the server to see if there has been some sort of state change, etc.), or any other monitoring technique known in the art. Such functionality may be advantageous when used in conjunction with systems that may not have been created with the intention of communicating with external systems, which is not uncommon in legacy healthcare information systems. The change events, including specific examples of change events, will be discussed in greater detail with respect to FIGS. 3 and 4, below.

The DAPA system 100 also comprises a transformation module 108. In the context of the present description and the claims that follow, a transformation module 108 is responsible for taking data objects from one data format, and placing them into another format. The use of a transformation module 108 is advantageous, as it allows the DAPA system 100 to integrate otherwise incompatible servers into a collaborative environment without requiring them to change the way they operate. According to various embodiments, the transformation module 108 comprises, or is communicatively coupled to, a transformation storage 118 that comprises a plurality of data format schema 120 that define the various formats that the DAPA system is "fluent" in. The transformation module 108 is able to use these schema to map one data format into another, translating the data from one server into a form that is understandable to another server/system.

In the context of the present description and the claims that follow, a data format may refer to a file type, but may also extend deeper, and describe the internal structure of a data object including, but not limited to, what data is expected, what form it is expected in (e.g. four digit year vs. two digit year, etc.), and the like.

In some embodiments, the transformation module 108 may be limited to simple mappings of one data field to another. In other embodiments, the transformation module 108 may be more sophisticated, allowing operations (e.g. transmutations, filters, regular expressions, etc.) to be defined within the schema 120 stored in the transformation storage 118. As a specific example, in an embodiment of the DAPA system 100 used to bridge a healthcare provider system with a healthcare payer system, the transformation module 108 may have a schema 120 that not only identifies the various data fields each system is expecting for a transaction requesting a determination on prior authorization for a surgical procedure, but also recognizes that these two organizations make use of different coding systems for describing surgical procedures. In this specific example, the schema 120 may include executable code, scripting language, or the like, that converts one coding system to another (e.g. looking up definitions in a third party server, looking up definitions in a code dictionary stored in the transformation storage 118, etc.).

The DAPA system 100 also comprises an intelligent automation module 106. In the context of the present description and the claims that follow, an intelligent automation module 106 is responsible for harnessing the abilities of the other modules to accomplish a particular task, or to react to an event or determination. While the other modules may have the ability to be configured to autonomously handle specific tasks, such as transforming a data object into another format, in some embodiments it is the intelligent automation module 106 that is directing the modules to work together towards a specific goal.

For example, the intelligent automation module 106 may instruct the authentication module 102 to establish a connection with a particular server, and then instruct the monitoring module 104 to observe that server until it determines that a change has occurred in a specific record (e.g. treatment plan for a particular patient in a hospital's EMR system, etc.). Upon detection of the change, the monitoring module 104 may retrieve the changed data from the server, which the intelligent automation module 106 may then instruct the transformation module 108 to manipulate until it is in a format compatible with another system (e.g. a medical insurance company's legacy system, etc.). A specific example of the use of a DAPA system 100 in a healthcare context will be discussed further with respect to FIG. 4, below.

In some embodiments, the intelligent automation module 106 may exist as a discrete executable. For example, in one embodiment, the intelligent automation module 106 may be a subroutine that is able to parse and execute code (e.g. a script, etc.) at runtime, allowing it to be quickly reconfigured. In other embodiments, the function performed by the intelligent automation module 106 may be split up among the other modules, each receiving the ability to determine what the overarching goal is (e.g. obtain a verification of benefits and coverage, etc.) and what their role is in that process. For example, a data wrapper may be used to identify what is being done, and which module is responsible for which step or stage.

As previously mentioned, the DAPA system 100 may be implemented in a variety of computing environments. In some embodiments, the DAPA system 100 may be implemented on a single device, while in other embodiments it may be implemented in a distributed environment making use of multiple devices operating in concert. In still other embodiments, the DAPA system 100 may be implemented in an abstracted environment, making use of virtual machines or containers, as is known in the art. In a particular embodiment, the DAPA system 100 may be implemented in a containerized environment, and one or more module may be instantiated as a separate container. Such an implementation may be advantageous in embodiments where the DAPA system 100 is used in conjunction with other systems that may benefit from the functionality of one or more modules (e.g. the monitoring module 104 could also be used to watch over the health or "heartbeat" of a high availability system that is distributed beyond a shared hardware environment, etc.)

Figure 2:
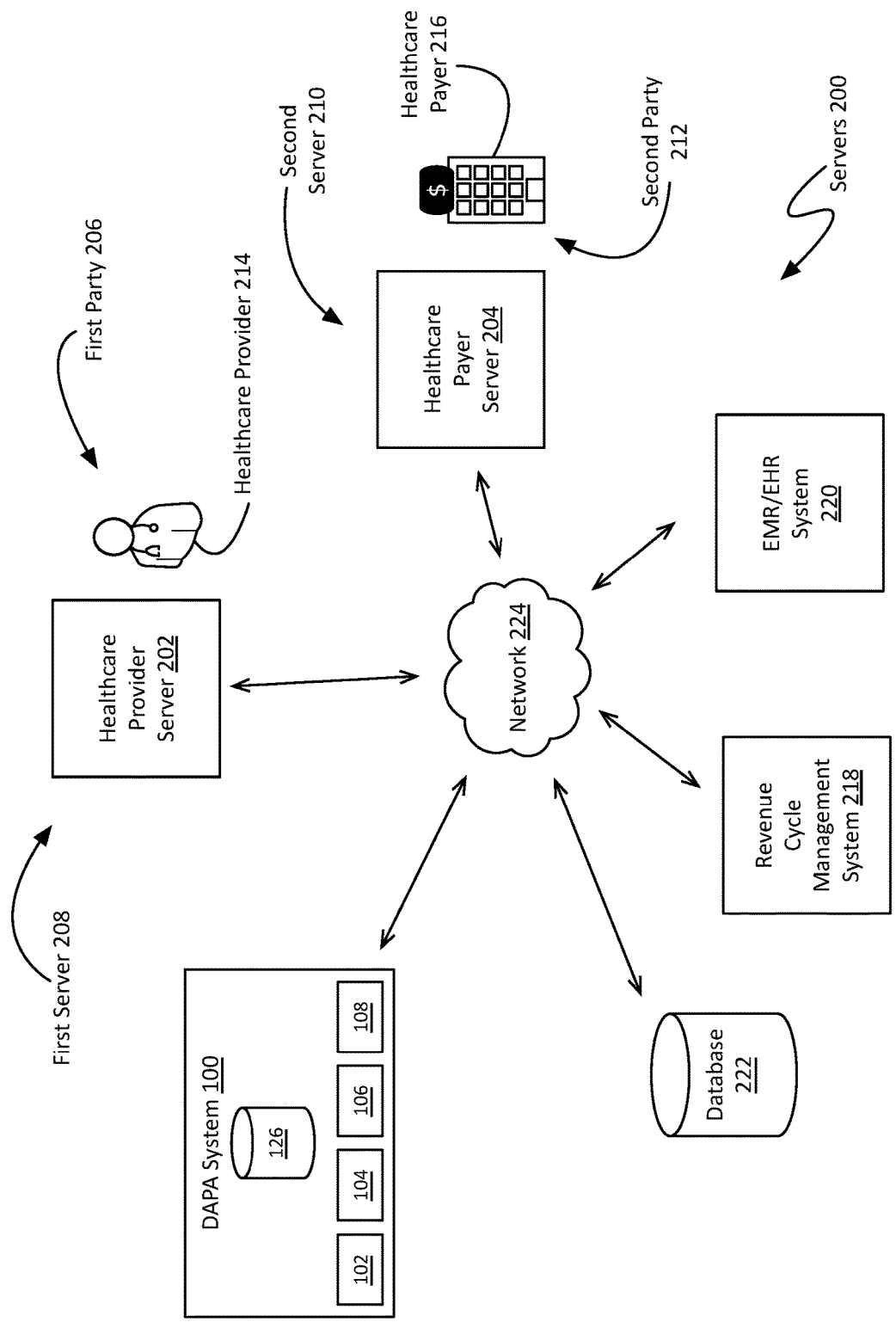
FIG. 2 is a network view of a DAPA system.

FIG. 2 is a network view of a non-limiting example of a DAPA system 100. As shown, the DAPA system 100 is communicatively coupled to a plurality of servers 200 through a network 224. The plurality of servers 200 includes a first server 208 associated with (e.g. under the control of, representing, owned by, etc.) a first party 206 and a second server 210 associated with a second party 212. Those skilled in the art will recognize that the term "server" could refer to a single, networked device, or could refer to a system of devices operating together and able to be accessed as a system over a network 224. In some embodiments, one or more of the servers coupled to the DAPA system 100 may be a database 222 or some other network accessible storage.

In the context of the present description and the claims that follow, a network 224 can be any framework that enables communication between servers. Examples include, but are not limited to, literal networks such as the Internet or other WAN or LAN implementations, as well as network overlays that abstract the inter-server communication beyond the physical network (e.g. a permissioned blockchain network, peer-to-peer networks, etc.). In some embodiments, a DAPA system 100 may be coupled to multiple networks, or types or interpretations of "network", at the same time.

FIG. 2 also provides a network view of a non-limiting example of a DAPA system 100 implemented in a healthcare context. As shown, the DAPA system 100 is coupled to a healthcare provider server 202 associated with a healthcare provider 214 (e.g. hospital, clinic, physician, pharmacy, laboratory, imaging center, etc.), as well as a healthcare payer server 204 associated with a healthcare payer 216 (e.g. medical insurance company, etc.). Examples of the types of servers a DAPA system 100 can be used with in a healthcare context include, but are not limited to, electronic medical record/electronic health record systems 220, revenue cycle management systems 218, and proprietary or legacy systems.

Figure 3:
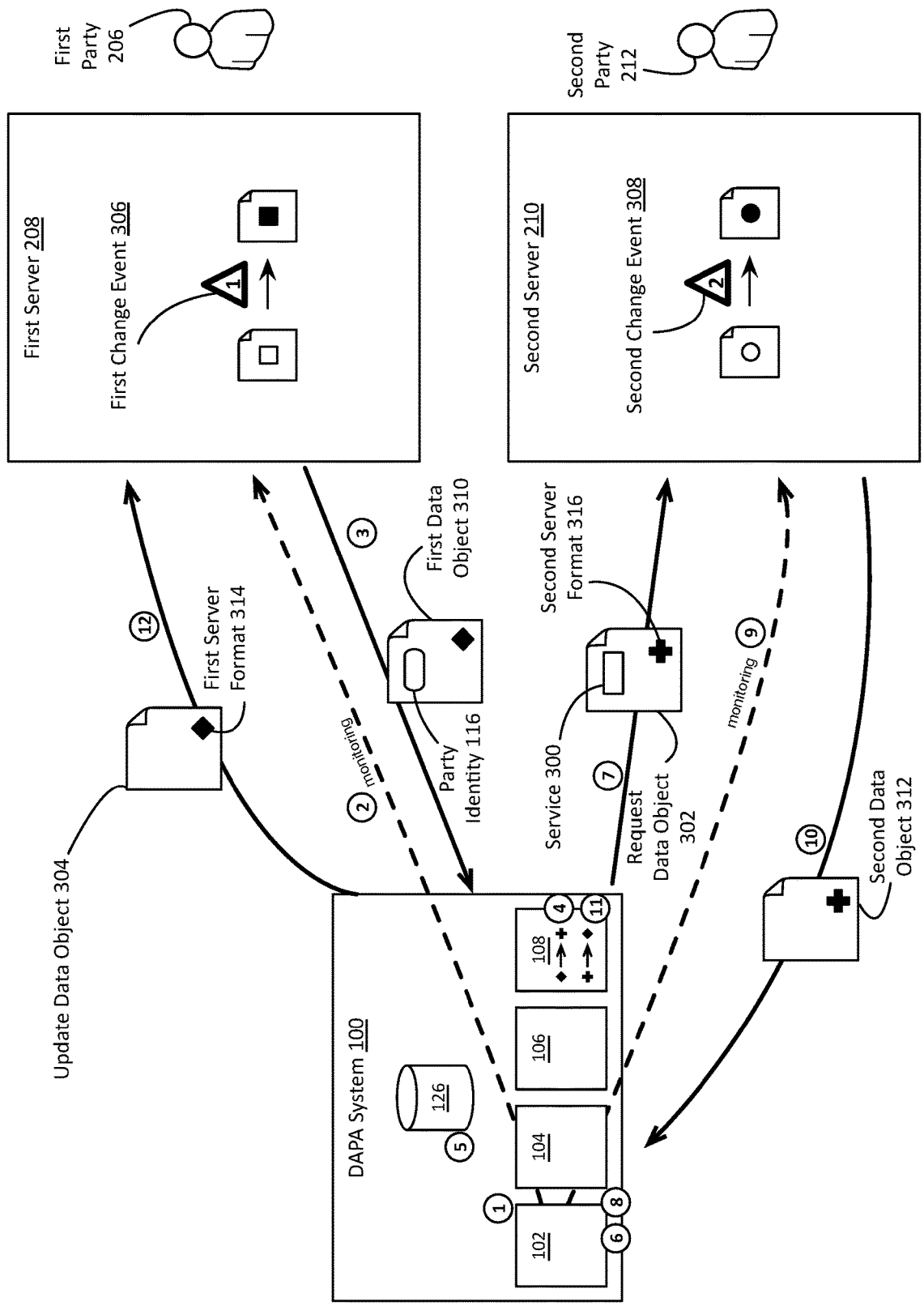
FIG. 3 is a network view of a process flow for data aggregation and process automation using a DAPA system.

FIG. 3 is a network view of a process flow for data aggregation and process automation using a non-limiting example of a DAPA system 100. Specifically, FIG. 3 shows a generalized, non-limiting example of a DAPA method, using a DAPA system 100, that makes a request of a second server 210 associated with a second party 212 after observing a change in a first server 208 associated with a first party 206. First, authenticated access to the first server 208 is obtained through the authentication module 102. See Circle '1'.

Once a connection has been established between the first server 208 and the DAPA system 100, the first server 208 is monitored by the monitoring module 104 for a first change event 306. See Circle '2'. In the context of the present description and the claims that follow, a change event is some change in state within a system or server. Examples include, but are not limited to, creation or deletion of a record or part of a record, modification of a record or part of a record, introduction or removal of hardware within the system being monitored, and the like. The scope of the monitoring may range from system-wide (e.g. any record within the system is modified, etc.) to highly specific (e.g. a change in a specified data field in a particular record, etc.).

Once the first change event 306 has been observed, the DAPA system 100 receives a first data object 310 from the first server 208 in a first server format 314. The first data object 310 includes, at the least, the identity 116 of the second party 212. See Circle '3'. In some embodiments, the observation of the first change event 306 may cause the DAPA system 100 to explicitly request the first data object 310 from the first server 208. In other embodiments, the act of monitoring the first server 208 for the first change event 306 may mean the DAPA system 100 has the first data object 310 (e.g. event detected by monitoring the value of what would become the first data object, etc.).

Next, the first data object 310 in the first server format 314 is transformed by the transformation module 108 into a request data object 302 in a second server format 316. See Circle '4'. The request data object 302 is based, at least in part, on information received in the first data object 310, and further specifies a service 300 that the DAPA system 100 is going to request the second server 210 provide. In the context of the present description and the claims that follow, a service 300 that is requested from a server may be any operation that the server is able to perform or cause to be performed (e.g. initiate review by a human agent, etc.). Examples include, but are not limited to, data retrieval, initiating a process or operation within the system that will return some sort of value or data object, perform an operation on data provided to the server, and the like.

Next, the intelligent automation module 106 identifies the second server 210 using the first data object 310 (e.g. using the party identity 116 from the first data object 310 in conjunction with the server records 111, resolving party identity 116 to routing information 114). See Circle '5'. Authenticated access is then established with the second server 210 through the authentication module 102. See Circle '6'.

Once a connection has been established and authenticated, the DAPA system 100 requests the service 300 from the second server 210 by submitting the request data object 302 to the second server 210. See Circle '7'. Next, if necessary, authenticated access is established again with the second server 210 (circle '8'), and the second server 210 is monitored by the monitoring module 104 for a second change event 308. See Circle '9'. The second change event 308 is an indication that the service 300 requested has been rendered (or, in some embodiments, has failed).

As a consequence of the second change event 308, the DAPA system 100 receives a second data object 312 in the second server format 316, similar to what happened after the first change event 306 while monitoring the first server 208. See Circle '10'.

In some embodiments, the results of the requested service 300 must be reported back to the first server 208, in the proper format. The transformation module 108 transforms the second data object 312 in the second server format 316 into an update data object 304 in the first server format 314. See Circle '11'. In some embodiments, the update data object 304 may include some or all of the data (reformatted for the first server 208) generated by the second server 210 while performing or rendering the requested service 300. Finally, the update data object 304 is submitted to the first server 208. See Circle '12'. Those skilled in the art will recognize that the non-limiting example of a DAPA method shown in FIG. 3 may be adapted for any number of industries, for the performance of a wide range of operations or services by one system/server/network on behalf of or acting on data from another system/server/network.

Those skilled in the art will recognize that DAPA methods and systems disclosed herein may be applied to almost any industry making use of proprietary systems or requiring cooperation between disparate computer systems. Healthcare, in particular, is an industry with a great need for DAPA. Healthcare requires the careful management of an ocean of information about patients, treatments, policies, regulations, and so forth. Each portion of the industry has, over time, developed standards for how that information is stored, managed, and used. These standards are not universal across healthcare. The systems used by healthcare payers are often not completely compatible with the systems used by healthcare providers, as discussed above.

The healthcare revenue cycle is a complicated and fragmented system involving a number different and often opposing organizations. Decisions that need to be made by one party often require information held by another, and the channels for requesting and providing such information can be frustratingly slow and unreliable. For example, prior authorization obtained through calling into a call center run by a healthcare payer 216 may result in an approval that is later disputed by the payer 216, with only the unrecorded verbal interaction to rely on. In other cases, the payer 216 may provide a web portal for asking if a patient has valid coverage, requiring a person to input the information manually to interact with the system. While seemingly a minor task, when required on the scale of a provider such as a hospital, the cost of inefficient communication methods like this can add up quickly. The process of determining what information is needed, requesting that information from another party, waiting for the information, receiving and evaluating it to finally render a decision often makes the process slow to a crawl, and provides many opportunities for problems and disagreements to arise.

By utilizing a DAPA system 100, the potentially incompatible legacy systems of healthcare providers and healthcare payers can work together in a quick and automated fashion, providing greater value to all parties involved and, ultimately, better care for the patient.

Figure 4:
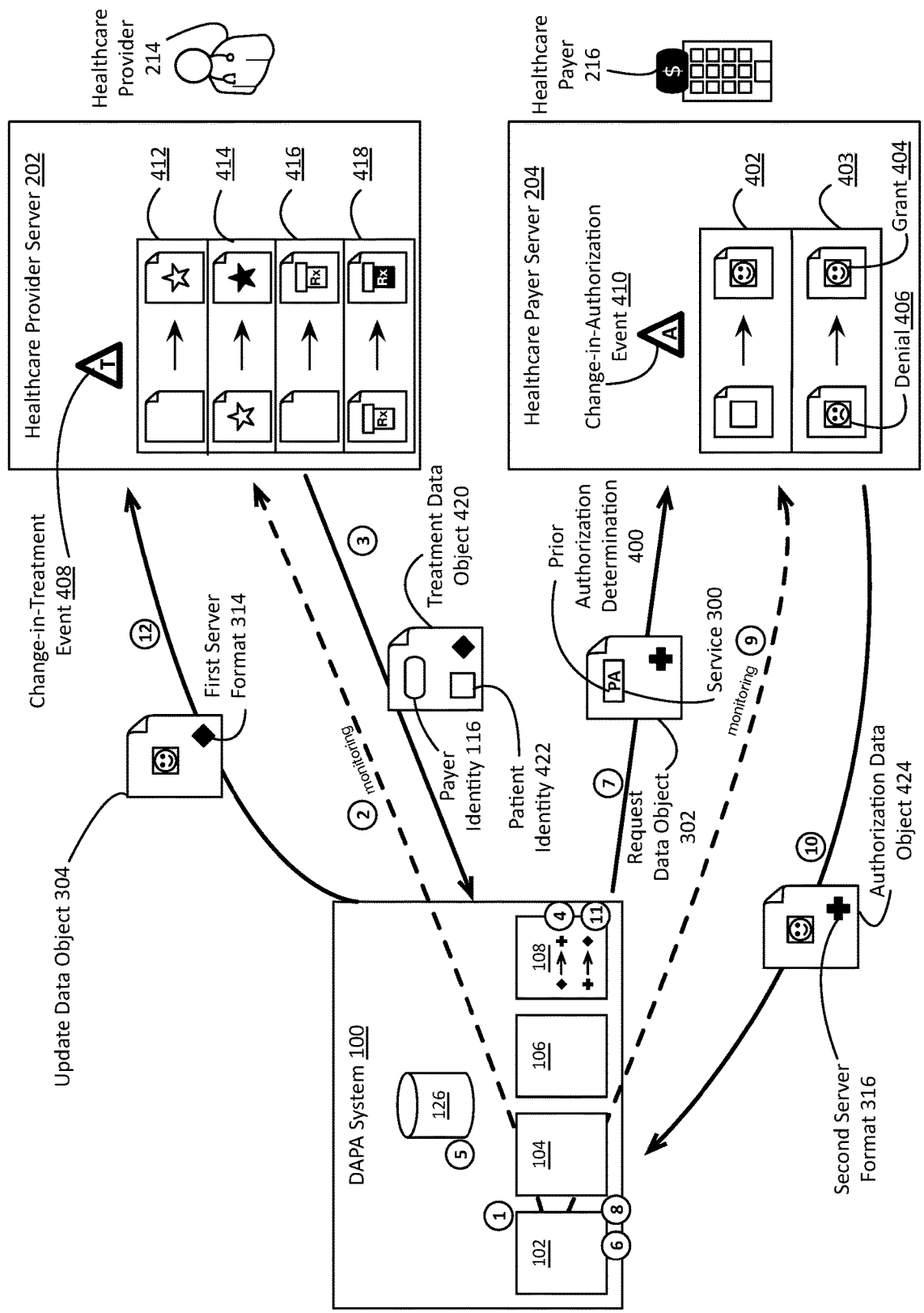
FIG. 4 is a network view of a process flow for an exemplary application of data aggregation and process automation using a DAPA system.

FIG. 4 is a network view of a process flow for data aggregation and process automation within a healthcare context, using a non-limiting example of a DAPA system 100. Specifically, FIG. 4 shows a non-limiting example of a DAPA method, using a DAPA system 100, being used to integrate systems used by a healthcare provider and healthcare payer, automating the process of requesting and obtaining prior authorization, a traditionally information-intensive and time consuming process.

First, authenticated access to the healthcare provider server 202 is obtained through the authentication module 102. See Circle '1'. Once a connection has been established between the healthcare provider server 202 and the DAPA system 100, the healthcare provider server 202 is monitored by the monitoring module 104 for a change-in-treatment event 408. See Circle '2'. In the context of the present description and the claims that follow, a change-in-treatment event is a change within a healthcare providers 214 system or server that indicates some sort of change in the treatment of a patient. For the purposes of prior authorization, exemplary events may include, but are not limited to, a new medical procedure 414, modification of a previously recorded procedure 414, a new prescription 416, and modification of a previously recorded prescription 418.

According to various embodiments, the scope of the monitoring may range from broad and system-wide (e.g. the DAPA system 100 will attempt to obtain prior authorization in response to a change-in-treatment event 408 for any patient, etc.) to the highly specific (e.g. the DAPA system 100 is monitoring for a change-in-treatment event 408 for a specific patient or patients associated with a specific healthcare payer 216, etc.).

Once a change-in-treatment event 408 has been observed, the DAPA system 100 receives a treatment data object 420 from the provider server 202 in a first server format 314 utilized by the payer server 202. The treatment data object 420 comprises, at the least, the identity 116 of the healthcare payer 216 associated with the patient, the patient identity 422, as well as information about the nature of the change in treatment. See Circle '3'. In the context of the present description and the claims that follow, a patient identity 422 can be any piece of data that can be used to uniquely identify a patient. Examples include, but are not limited to, a full name, a social security number, a patient identification number, and the like.

In some embodiments, the observation of the change-in-treatment event 408 may cause the DAPA system 100 to explicitly request the treatment data object 420 from the healthcare provider server 202. In other embodiments, the act of monitoring the healthcare provider server 202 for the change-in-treatment event 408 may mean the DAPA system 100 has the treatment data object 420 (e.g. event detected by monitoring the value of what would become the treatment data object, etc.).

Next, the treatment data object 420 in the first server format 314 is transformed by the transformation module 108 into a request data object 302 in a second server format 316. See Circle '4'. The request data object 302 is based, at least in part, on information received in the treatment data object 420, and further specifies a service 300 that the DAPA system 100 is requesting from the healthcare payer server 204. Examples of services in the healthcare context include, but are not limited to, prior authorization determination 400, verification of benefits and coverage, and the like. In this specific example, the service 300 being requested is a prior authorization determination 400.

Next, the intelligent automation module 106 automatically identifies the healthcare payer server 204 using the treatment data object 420 (e.g. using the party identity 116 from the treatment data object 420 in conjunction with the server records 111 resolving party identity 116 to routing information 114, etc.). See Circle '5'. Authenticated access is then established with the healthcare payer server 204 through the authentication module 102. See Circle '6'.

Once a connection has been established and authenticated, the DAPA system 100 requests a prior authorization determination 400 from the healthcare payer server 204 by submitting the request data object 302 to the healthcare payer server 204. See Circle '7'. Next, if necessary, authenticated access is established again with the healthcare payer server 204 (circle '8'), and the healthcare payer server 204 is monitored by the monitoring module 104 for a change-in-authorization event 410. See Circle '9'. In the context of the present description and the claims that follow a change-in-authorization event is a change within a healthcare payers 216 system or server that indicates a change in the authorization for a specific healthcare expense. Examples may include, but are not limited to, a new authorization decision 402 and a modified authorization decision 403 (e.g. the result of an appeal of a previous decision, etc.). The change-in-authorization event 410 is an indication that the service 300 requested has been rendered by the healthcare payer 216.

As a consequence of the change-in-authorization event 410, the DAPA system 100 receives a authorization data object 424 in the second server format 316, similar to what happened after the change-in-treatment event 408 while monitoring the healthcare provider server 202. See Circle '10'.

The results of the prior authorization determination 400 are reported back to the healthcare provider server 202, in the proper format. The transformation module 108 transforms the authorization data object 424 in the second server format 316 into an update data object 304 in the first server format 314. See Circle '11'. In some embodiments, the update data object 304 may include some or all of the data (reformatted for the healthcare provider server 202) generated by the healthcare payer server 204 while making the prior authorization determination 400. Finally, the update data object 304 is submitted to the healthcare provider server 202. See Circle '12'. In some embodiments, the results of the determination may also be automatically communicated to the patient, as well.

Figure 5:
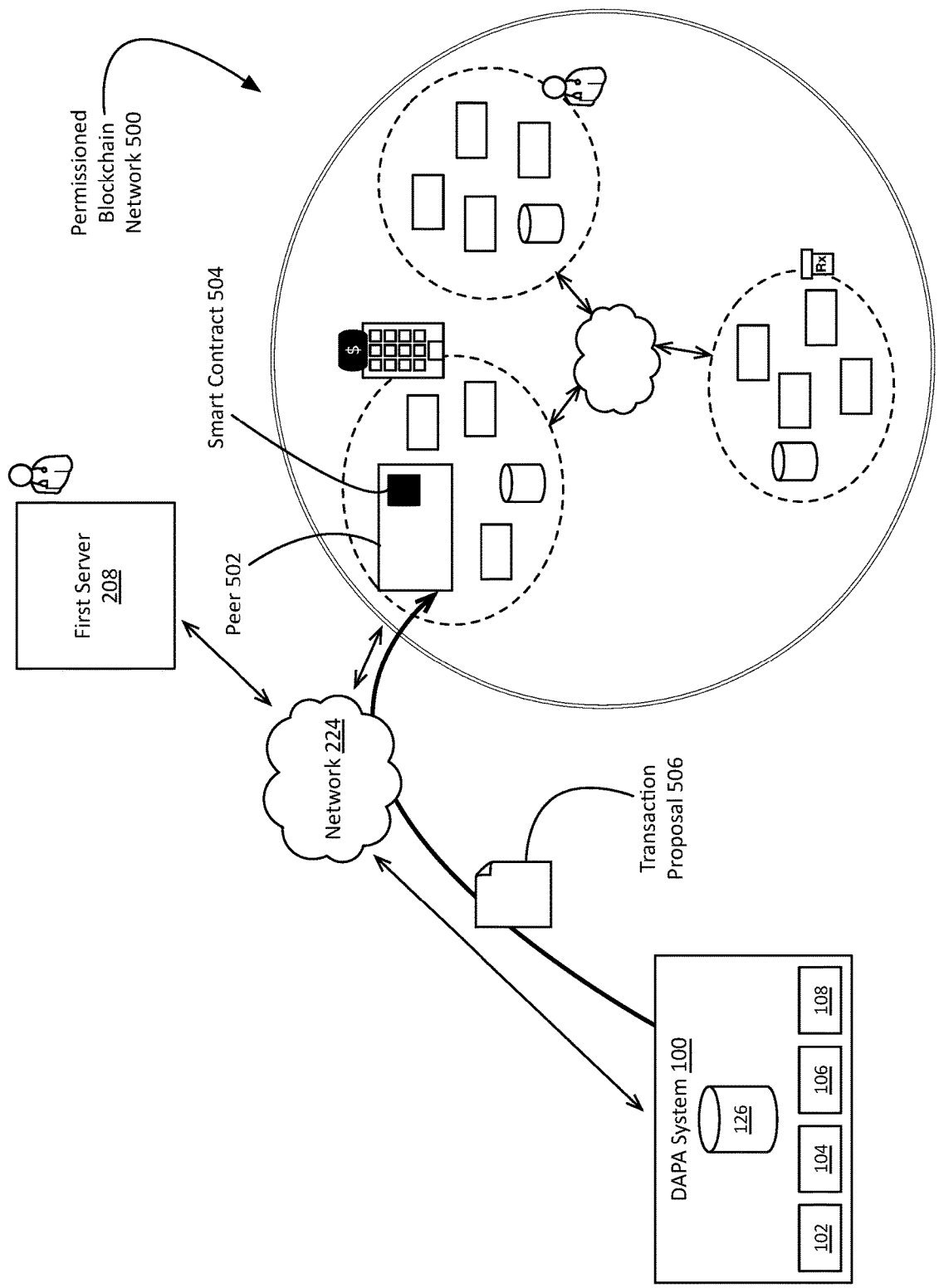
FIG. 5 is a network view of a DAPA system used in conjunction with a permissioned blockchain network.

As discussed above, a DAPA system 100 may be used to integrate multiple systems using disparate data formats and protocols. According to various embodiments, a DAPA system 100 may also bridge systems that exist in, or make use of, different networks. FIG. 5 is a network view of a DAPA system 100 used in conjunction with a permissioned blockchain network 500. The use of permissioned blockchain networks 500 in healthcare provides many advantages, including allowing parties with diverging business interests (e.g. providers vs. payers, etc.) to interact in a way that keeps everyone honest by recording all transactions in an immutable transaction history visible to all participating organizations, as is known in the art.

A DAPA system 100 used in conjunction with a permissioned blockchain network 500 does not differ greatly from other implementations. As shown in FIG. 5, the DAPA system 100 is communicatively coupled to a peer 502 associated with an authorized organization participating in the permissioned blockchain network 500, similar to being coupled to a second server 210 associated with a second party 212. As an option, the submission of a data object (e.g. first data object 310, request data object 302, etc.) to the peer 502 may comprise the invocation of a smart contract 504 within the blockchain network 500 through the submission of a transaction proposal 506 through the peer 502. As an option, the invocation of a smart contract 504 may be initiated by the intelligent automation module 106, according to various embodiments. The ability to invoke smart contracts 504 with the DAPA system 100 is advantageous, as the smart contracts 504 provide another means of automating various processes within and adjacent to (e.g. a communicatively coupled server outside the blockchain network, etc.) the blockchain network 500.

Figure 6:
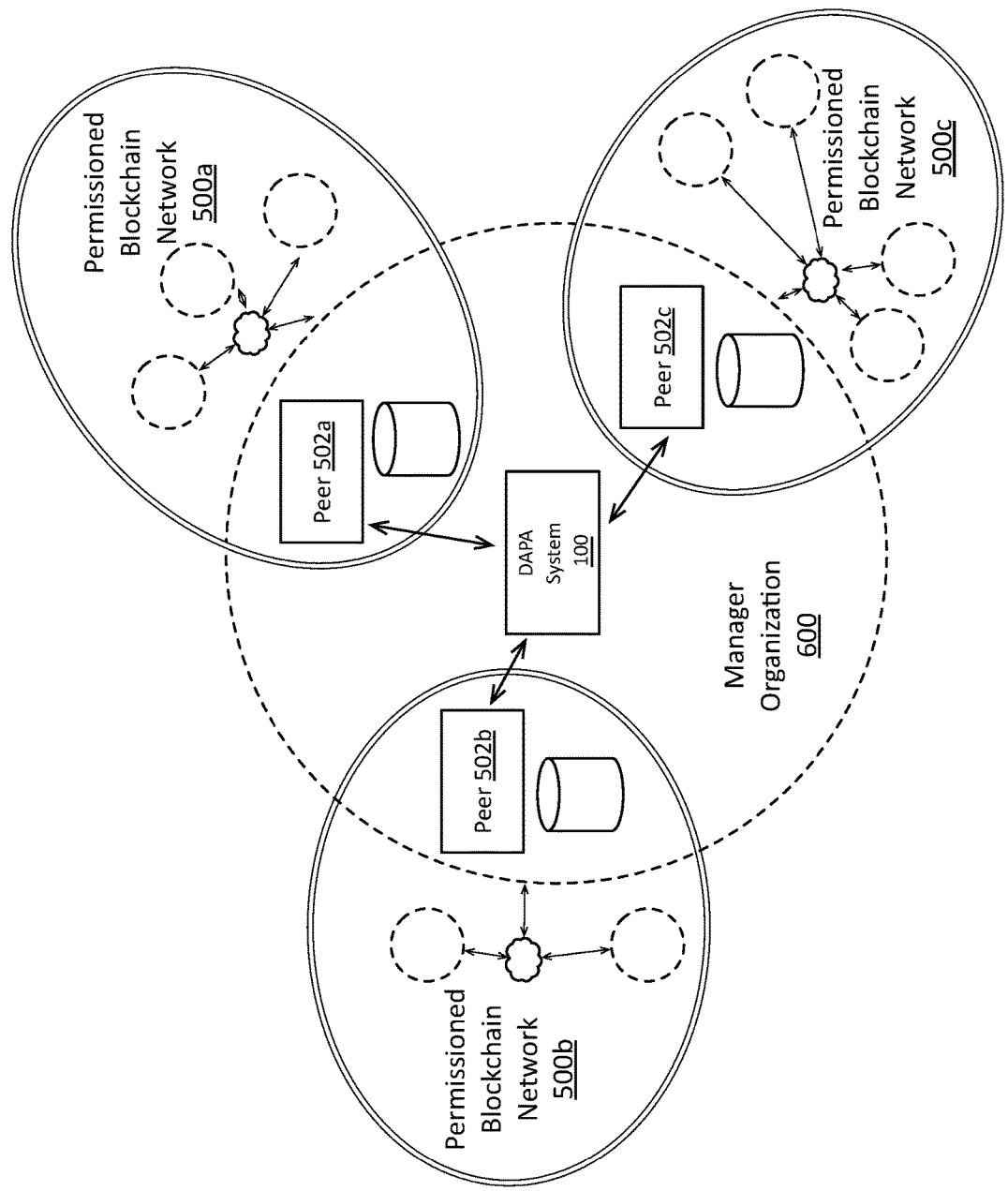
FIG. 6 is a network view of a DAPA system used to bridge multiple permissioned blockchain networks.

FIG. 6 is a network view of multiple blockchain networks 500a-c being bridged by a manger organization 600, using a DAPA system 100 as an interface between the networks. As shown, multiple blockchain networks could be linked to share information by a manager organization 600 that maintains a peer 502 (or multiple peers) within each network. The transactions and requests received by each peer 502 are passed through the DAPA system 100, which may be configured to determine which network to pass the request to, and reconfigure the information to be compatible with the protocols of said network. There are many advantages to be had with the aggregation of more information. Using DAPA systems 100 to bridge blockchain networks 500, each comprising multiple data-rich organizations, rapidly increases the available data with little additional overhead or reconfiguration.

Figure 7:
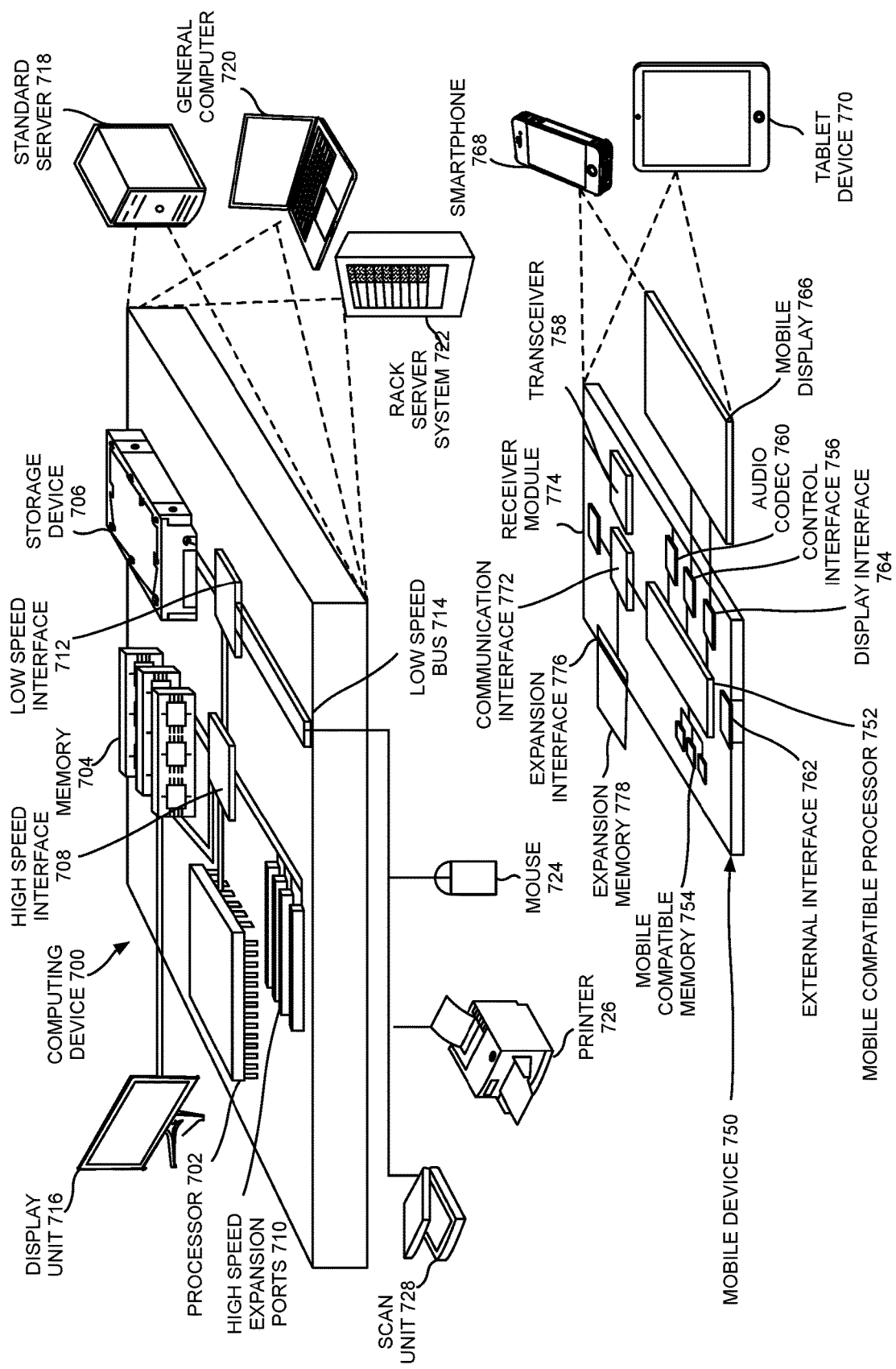
FIG. 7 is a schematic diagram of a specific computing device that can be used to implement the methods and systems disclosed herein.

FIG. 7 is a schematic diagram of specific computing device 700 and a specific mobile computing device 750 that can be used to perform and/or implement any of the embodiments disclosed herein. In one or more embodiments, DAPA system 100 of FIG. 1 as a whole, or one or more individual modules 102-108 of FIG. 1, or a containerized environment hosting some or all elements of FIGS. 1-4, may be implemented in the specific computing device 700.

The specific computing device 700 may represent various forms of digital computers, such as laptops, desktops, workstations, personal digital assistants, servers, blade servers, mainframes, and/or other appropriate computers. The specific mobile computing device 730 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 700 may include a processor 703, a memory 705, a storage device 706, a high speed interface 708 coupled to the memory 705 and a plurality of high speed expansion ports 710, and a low speed interface 712 coupled to a low speed bus 714 and a storage device 706. In one embodiment, each of the components heretofore may be inter-coupled using various buses, and may be mounted on a common motherboard and/or in other manners as appropriate. The processor 703 may process instructions for execution in the specific computing device 700, including instructions stored in the memory 705 and/or on the storage device 706 to display a graphical information for a GUI on an external input/output device, such as a display unit 716 coupled to the high speed interface 708, according to one embodiment.

In other embodiments, multiple processors and/or multiple buses may be used, as appropriate, along with multiple memories and/or types of memory. Also, a plurality of specific computing device 700 may be coupled with, with each device providing portions of the necessary operations (e.g., as a server bank, a group of blade servers, and/or a multi-processor system).

The memory 705 may be coupled to the specific computing device 700. In one embodiment, the memory 705 may be a volatile memory. In another embodiment, the memory 705 may be a non-volatile memory. The memory 705 may also be another form of computer-readable medium, such as a magnetic and/or an optical disk. The storage device 706 may be capable of providing mass storage for the specific computing device 700. In one embodiment, the storage device 706 may be includes a floppy disk device, a hard disk device, an optical disk device, a tape device, a flash memory and/or other similar solid state memory device. In another embodiment, the storage device 706 may be an array of the devices in a computer-readable medium previously mentioned heretofore, computer-readable medium, such as, and/or an array of devices, including devices in a storage area network and/or other configurations.

A computer program may be comprised of instructions that, when executed, perform one or more methods, such as those described above. The instructions may be stored in the memory 705, the storage device 706, a memory coupled to the processor 703, and/or a propagated signal.

The high speed interface 708 may manage bandwidth-intensive operations for the specific computing device 700, while the low speed interface 712 may manage lower bandwidth-intensive operations. Such allocation of functions is exemplary only. In one embodiment, the high speed interface 708 may be coupled to the memory 705, the display unit 716 (e.g., through a graphics processor and/or an accelerator), and to the plurality of high speed expansion ports 710, which may accept various expansion cards.

In the embodiment, the low speed interface 712 may be coupled to the storage device 706 and the low speed bus 714. The low speed bus 714 may be comprised of a wired and/or wireless communication port (e.g., a Universal Serial Bus ("USB"), a Bluetooth® port, an Ethernet port, and/or a wireless Ethernet port). The low speed bus 714 may also be coupled to the scan unit 728, a printer 726, a keyboard, a mouse 724, and a networking device (e.g., a switch and/or a router) through a network adapter.

The specific computing device 700 may be implemented in a number of different forms, as shown in the figure. In one embodiment, the specific computing device 700 may be implemented as a standard server 718 and/or a group of such servers. In another embodiment, the specific computing device 700 may be implemented as part of a rack server system 722. In yet another embodiment, the specific computing device 700 may be implemented as a general computer 720 such as a laptop or desktop computer. Alternatively, a component from the specific computing device 700 may be combined with another component in a specific mobile computing device 730. In one or more embodiments, an entire system may be made up of a plurality of specific computing device 700 and/or a plurality of specific computing device 700 coupled to a plurality of specific mobile computing device 730.

In one embodiment, the specific mobile computing device 730 may include a mobile compatible processor 732, a mobile compatible memory 734, and an input/output device such as a mobile display 746, a communication interface 752, and a transceiver 738, among other components. The specific mobile computing device 730 may also be provided with a storage device, such as a microdrive or other device, to provide additional storage. In one embodiment, the components indicated heretofore are inter-coupled using various buses, and several of the components may be mounted on a common motherboard.

The mobile compatible processor 732 may execute instructions in the specific mobile computing device 730, including instructions stored in the mobile compatible memory 734. The mobile compatible processor 732 may be implemented as a chipset of chips that include separate and multiple analog and digital processors. The mobile compatible processor 732 may provide, for example, for coordination of the other components of the specific mobile computing device 730, such as control of user interfaces, applications run by the specific mobile computing device 730, and wireless communication by the specific mobile computing device 730.

The mobile compatible processor 732 may communicate with a user through the control interface 736 and the display interface 744 coupled to a mobile display 746. In one embodiment, the mobile display 746 may be a Thin-Film-Transistor Liquid Crystal Display ("TFT LCD"), an Organic Light Emitting Diode ("OLED") display, and another appropriate display technology. The display interface 744 may comprise appropriate circuitry for driving the mobile display 746 to present graphical and other information to a user. The control interface 736 may receive commands from a user and convert them for submission to the mobile compatible processor 732.

In addition, an external interface 742 may be provide in communication with the mobile compatible processor 732, so as to enable near area communication of the specific mobile computing device 730 with other devices. External interface 742 may provide, for example, for wired communication in some embodiments, or for wireless communication in other embodiments, and multiple interfaces may also be used.

The mobile compatible memory 734 may be coupled to the specific mobile computing device 730. The mobile compatible memory 734 may be implemented as a volatile memory and a non-volatile memory. The expansion memory 758 may also be coupled to the specific mobile computing device 730 through the expansion interface 756, which may comprise, for example, a Single In Line Memory Module ("SIMM") card interface. The expansion memory 758 may provide extra storage space for the specific mobile computing device 730, or may also store an application or other information for the specific mobile computing device 730.

Specifically, the expansion memory 758 may comprise instructions to carry out the processes described above. The expansion memory 758 may also comprise secure information. For example, the expansion memory 758 may be provided as a security module for the specific mobile computing device 730, and may be programmed with instructions that permit secure use of the specific mobile computing device 730. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 734, the expansion memory 758, a memory coupled to the mobile compatible processor 732, and a propagated signal that may be received, for example, over the transceiver 738 and/or the external interface 742.

The specific mobile computing device 730 may communicate wirelessly through the communication interface 752, which may be comprised of a digital signal processing circuitry. The communication interface 752 may provide for communications using various modes and/or protocols, such as, a Global System for Mobile Communications ("GSM") protocol, a Short Message Service ("SMS") protocol, an Enhanced Messaging System ("EMS") protocol, a Multimedia Messaging Service ("MMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 738 (e.g., radio-frequency transceiver). In addition, short-range communication may occur, such as using a Bluetooth®, Wi-Fi, and/or other such transceiver. In addition, a GPS ("Global Positioning System") receiver module 754 may provide additional navigation-related and location-related wireless data to the specific mobile computing device 730, which may be used as appropriate by a software application running on the specific mobile computing device 730.

The specific mobile computing device 730 may also communicate audibly using an audio codec 740, which may receive spoken information from a user and convert it to usable digital information. The audio codec 740 may likewise generate audible sound for a user, such as through a speaker (e.g., in a handset smartphone of the specific mobile computing device 730). Such a sound may comprise a sound from a voice telephone call, a recorded sound (e.g., a voice message, a music files, etc.) and may also include a sound generated by an application operating on the specific mobile computing device 730.

The specific mobile computing device 730 may be implemented in a number of different forms, as shown in the figure. In one embodiment, the specific mobile computing device 730 may be implemented as a smartphone 748. In another embodiment, the specific mobile computing device 730 may be implemented as a personal digital assistant ("PDA"). In yet another embodiment, the specific mobile computing device, 730 may be implemented as a tablet device 750.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other modules, data objects, formats, and the like could be intermixed or substituted with those provided. In places where the description above refers to particular embodiments of data aggregation and process automation systems and methods, it should be readily apparent that a number of modifications may be made without departing from the spirit thereof and that these embodiments and implementations may be applied to other data aggregation and process automation systems and methods as well. Accordingly, the disclosed subject matter is intended to embrace all such alterations, modifications and variations that fall within the spirit and scope of the disclosure and the knowledge of one of ordinary skill in the art.

What is claimed is:

1. A data aggregation and process automation (DAPA) system, comprising:

an authentication module configured to initiate authenticated communication with a plurality of servers communicatively coupled to the DAPA system, the authentication module comprising an authentication storage having a plurality of authentication credentials and routing information for each of the plurality of servers, each of the plurality of servers associated with a different party, the plurality of servers comprising a healthcare provider server associated with a healthcare provider and a healthcare payer server associated with a healthcare payer;

a monitoring module configured to monitor the provider server for a change-in-treatment event after receiving authenticated access to the provider server through the authentication module, and further configured to monitor the payer server for a change-in-authorization event after receiving authenticated access to the payer server through the authentication module, wherein the change-in-treatment event is the entry of one of a new medical procedure, a modified medical procedure, a new prescription, and a modified prescription in the provider server and results in the receipt of a treatment data object in a first server format utilized by the provider server, wherein the change-in-authorization event results in the receipt of an authorization data object in a second server format utilized by the payer server, and wherein the treatment data object identifies the healthcare payer and comprises a patient identity;

an intelligent automation module configured to:

automatically identify the payer server using the treatment data object and the authentication storage in response to the receipt of the treatment data object by the monitoring module, establish authenticated access to the payer server using the authentication module, request a prior authorization determination from the payer server by submitting a request data object comprising at least the patient identity, wherein said request data object is in the second server format and is based on the treatment data object, and automatically submit an update data object to the provider server in response to the receipt of the authorization data object by the monitoring module, said update data object being in the first server format, based on the authorization data object, and indicating one of a grant of prior authorization and a denial of prior authorization; and a transformation module comprising a transformation storage having a plurality of data format schema comprising a first server format schema describing the first server format utilized by the provider server and a second server format schema describing the second server format utilized by the payer server, the transformation module configured to transform the treatment data object in the first server format into the request data object in the second server format, and further configured to transform the authorization data object in the second server format into the update data object in the first server format.

2. The DAPA system of claim 1, wherein at least one of the provider server and the payer server is a peer on a permissioned blockchain network.

3. The DAPA system of claim 2, wherein the intelligent automation module is further configured to invoke a smart contract within the permissioned blockchain network.

4. The DAPA system of claim 1, wherein the DAPA system is executed within a containerized computing environment.

5. The DAPA system of claim 1, wherein the authentication storage and the transformation storage exist within the same database.

6. The DAPA system of claim 1, wherein the monitoring module is configured to monitor the provider server and the payer server using at least one of long polling, publication/subscription messaging, and periodic queries.

7. The DAPA system of claim 1, wherein at least one of the provider server and the payer server is one of a revenue cycle management system, an electronic medical record system, an electronic health record system, and a database.

8. A data aggregation and process automation (DAPA) system, comprising:

an authentication module configured to initiate authenticated communication with a plurality of servers communicatively coupled to the DAPA system, the authentication module comprising an authentication storage having a plurality of authentication credentials and routing information for each of the plurality of servers, each of the plurality of servers associated with a different party, the plurality of servers comprising a first server associated with a first party and a second server associated with a second party;

a monitoring module configured to monitor the first server for a first change event after receiving authenticated access to the first server through the authentication module, and further configured to monitor the second server for a second change event after receiving authenticated access to the second server through the authentication module, wherein the first change event is the entry of one of a new medical procedure, a modified medical procedure, a new prescription, and a modified prescription in the first server and results in the receipt of a first data object in a first server format utilized by the first server, wherein the second change event results in the receipt of a second data object in a second server format utilized by the second server, and wherein the first data object identifies the second party and comprises a patient identity;

an intelligent automation module configured to:

automatically identify the second server using the first data object and the authentication storage in response to the receipt of the first data object by the monitoring module, establish authenticated access to the second server through the authentication module, request a service from the second server by submitting a request data object comprising the patient identity, wherein said request data object being in the second server format and based on the first data object, and wherein the service requested from the second server is one of a prior authorization determination and a verification of benefits and coverage, and automatically submit an update data object to the first server in response to the receipt of the second data object by the monitoring module, said update data object being in the first server format and based on the second data object; and a transformation module comprising a transformation storage having a plurality of data format schema comprising a first server format schema and a second server format schema, the transformation module configured to transform the first data object in the first server format into the request data object in the second server format, and further configured to transform the second data object in the second server format into the update data object in the first server format;

wherein the first party is a healthcare provider and the second party is a healthcare payer.

9. The DAPA system of claim 8, wherein at least one of the first server and the second server is a peer on a permissioned blockchain network.

10. The DAPA system of claim 9, wherein the intelligent automation module is further configured to invoke a smart contract within the permissioned blockchain network.

11. The DAPA system of claim 8, wherein the DAPA system is executed within a containerized computing environment.

12. The DAPA system of claim 8, wherein the authentication storage and the transformation storage exist within the same database.

13. The DAPA system of claim 8, wherein the monitoring module is configured to monitor the first server and the second server using at least one of long polling, publication/subscription messaging, and periodic queries.

14. The DAPA system of claim 8, wherein at least one of the first server and the second server is one of a revenue cycle management system, an electronic medical record system, an electronic health record system, and a database.

15. A data aggregation and process automation (DAPA) system, comprising:

an authentication module configured to initiate authenticated communication with a plurality of servers communicatively coupled to the DAPA system, the authentication module comprising an authentication storage having a plurality of authentication credentials and routing information for each of the plurality of servers, each of the plurality of servers associated with a different party, the plurality of servers comprising a first server associated with a first party and a second server associated with a second party;

a monitoring module configured to monitor the first server for a first change event after receiving authenticated access to the first server through the authentication module, and further configured to monitor the second server for a second change event after receiving authenticated access to the second server through the authentication module, wherein the first change event results in the receipt of a first data object in a first server format and the second change event results in the receipt of a second data object in a second server format, and wherein the first data object identifies the second party;

an intelligent automation module configured to:
automatically identify the second server using the first data object and the authentication storage in response to the receipt of the first data object by the monitoring module,
establish authenticated access to the second server through the authentication module,
request a service from the second server by submitting a request data object, said request data object being in the second server format and based on the first data object, and
automatically submit an update data object to the first server in response to the receipt of the second data object by the monitoring module, said update data object being in the first server format and based on the second data object; and a transformation module comprising a transformation storage having a plurality of data format schema comprising a first server format schema and a second server format schema, the transformation module configured to transform the first data object in the first server format into the request data object in the second server format, and further configured to transform the second data object in the second server format into the update data object in the first server format.

16. The DAPA system of claim 15, wherein the monitoring module is configured to monitor the first server and the second server using at least one of long polling, publication/subscription messaging, and periodic queries.

17. The DAPA system of claim 15, wherein at least one of the first server and the second server is a peer on a permissioned blockchain network.

18. The DAPA system of claim 17, wherein the intelligent automation module is further configured to invoke a smart contract within the permissioned blockchain network.

19. The DAPA system of claim 15, wherein the first data object comprises a patient identity.

20. The DAPA system of claim 19, wherein the service requested from the second server is a prior authorization determination, and wherein the request data comprises the patient identity.

* * * * *